(12) United States Patent
Kieser et al.

(10) Patent No.: US 10,682,204 B2
(45) Date of Patent: Jun. 16, 2020

(54) METHOD OF PRODUCING AN ELONGATE IMPLANT CONTAINING A STRUCTURALLY ENCODED PIN THROUGH ELECTRICAL DISCHARGE MACHINING

(71) Applicants: Brian Kieser, San Antonio, TX (US); Thomas Zink, San Antonio, TX (US); Nicholas M. Cordaro, Vista, CA (US)

(72) Inventors: Brian Kieser, San Antonio, TX (US); Thomas Zink, San Antonio, TX (US); Nicholas M. Cordaro, Vista, CA (US)

( * ) Notice: Subject to any disclaimer, the term of this patent is extended or adjusted under 35 U.S.C. 154(b) by 286 days.

(21) Appl. No.: 15/806,548

(22) Filed: Nov. 8, 2017

(65) Prior Publication Data

US 2018/0064507 A1    Mar. 8, 2018

Related U.S. Application Data

(63) Continuation-in-part of application No. 15/403,063, filed on Jan. 10, 2017, now Pat. No. 10,152,661,
(Continued)

(51) Int. Cl.
*A61B 90/96* (2016.01)
*A61B 17/86* (2006.01)
(Continued)

(52) U.S. Cl.
CPC .............. *A61B 90/96* (2016.02); *A61B 17/70* (2013.01); *A61B 17/7002* (2013.01); *A61B 17/7032* (2013.01); *A61B 17/864* (2013.01); *A61B 17/865* (2013.01); *A61B 17/866* (2013.01); *A61B 17/8685* (2013.01); *A61B 50/20* (2016.02); *A61B 50/22* (2016.02); *A61B 50/30* (2016.02); *A61B 50/33* (2016.02); *A61B 50/34* (2016.02); *A61B 90/39* (2016.02); *A61B 90/90* (2016.02); *A61B 90/98* (2016.02); *B33Y 80/00* (2014.12); *G06K 7/1413* (2013.01); *G06K 19/06* (2013.01); *A61B 5/06* (2013.01); *A61B 6/12* (2013.01); *A61B 8/0841* (2013.01); *A61B 2017/00526* (2013.01); *A61B 2050/3008* (2016.02); *A61B 2050/3011* (2016.02);
(Continued)

(58) Field of Classification Search
CPC .............................. A61B 90/90; A61B 17/865
See application file for complete search history.

(56) References Cited

U.S. PATENT DOCUMENTS

| 6,149,653 A | * | 11/2000 | Deslauriers | ........ | A61B 17/0401 |
| | | | | | 606/232 |
| 8,136,728 B2 | * | 3/2012 | Turner | ...................... | A61L 2/07 |
| | | | | | 235/385 |

* cited by examiner

*Primary Examiner* — Andrew Yang
(74) *Attorney, Agent, or Firm* — Brennan, Manna & Diamond, LLC

(57) ABSTRACT

An implant and method for manufacturing an implant comprising an implant body defining a longitudinal axis and a structurally encoded pin contained within the implant body and aligned substantially along the longitudinal axis, the structurally encoded pin having a shape or surface characteristics discernable by an imaging modality such as x-ray, fluoroscopy, computed tomography, electromagnetic radiation, ultrasound, visible light, UV light, magnetic resonance imaging, positron emission tomography and neutron imaging, from outside the implant body, the shape or surface characteristics representing structurally encoded data. The structurally encoded pin is encoded via an electric discharge machining process.

15 Claims, 15 Drawing Sheets

Related U.S. Application Data which is a continuation-in-part of application No. 15/243,036, filed on Aug. 22, 2016, and a continuation-in-part of application No. 15/243,036, filed on Aug. 22, 2016, which is a continuation-in-part of application No. 14/823,234, filed on Aug. 11, 2015, now Pat. No. 9,424,503, and a continuation-in-part of application No. 14/456,665, filed on Aug. 11, 2014, now Pat. No. 9,943,378.

(60) Provisional application No. 62/419,341, filed on Nov. 8, 2016, provisional application No. 62/419,373, filed on Nov. 8, 2016, provisional application No. 62/419,364, filed on Nov. 8, 2016, provisional application No. 62/419,353, filed on Nov. 8, 2016, provisional application No. 62/035,875, filed on Aug. 11, 2014, provisional application No. 61/938,475, filed on Feb. 11, 2014.

(51) Int. Cl.
| | |
|---|---|
| *A61B 90/00* | (2016.01) |
| *G06K 7/14* | (2006.01) |
| *A61B 90/98* | (2016.01) |
| *B33Y 80/00* | (2015.01) |
| *A61B 17/70* | (2006.01) |
| *A61B 50/33* | (2016.01) |
| *A61B 50/30* | (2016.01) |
| *A61B 50/20* | (2016.01) |
| *G06K 19/06* | (2006.01) |
| *A61B 50/22* | (2016.01) |
| *A61B 90/90* | (2016.01) |
| *A61B 50/34* | (2016.01) |
| *A61B 8/08* | (2006.01) |
| *B29L 31/00* | (2006.01) |
| *A61B 5/06* | (2006.01) |
| *A61B 6/12* | (2006.01) |
| *A61B 17/00* | (2006.01) |

(52) U.S. Cl.
CPC ... *A61B 2090/373* (2016.02); *A61B 2090/374* (2016.02); *A61B 2090/378* (2016.02); *A61B 2090/3762* (2016.02); *A61B 2090/3925* (2016.02); *A61B 2090/3937* (2016.02); *A61B 2090/3954* (2016.02); *A61B 2090/3966* (2016.02); *A61F 2250/0086* (2013.01); *A61F 2250/0089* (2013.01); *B29K 2995/0056* (2013.01); *B29L 2031/7532* (2013.01); *G06K 2019/06271* (2013.01)

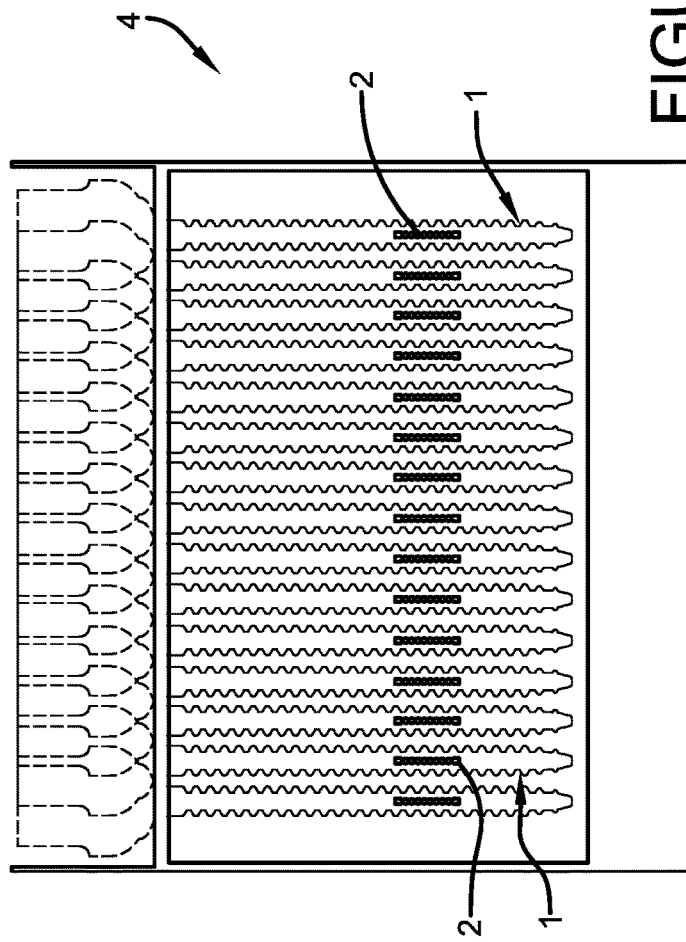
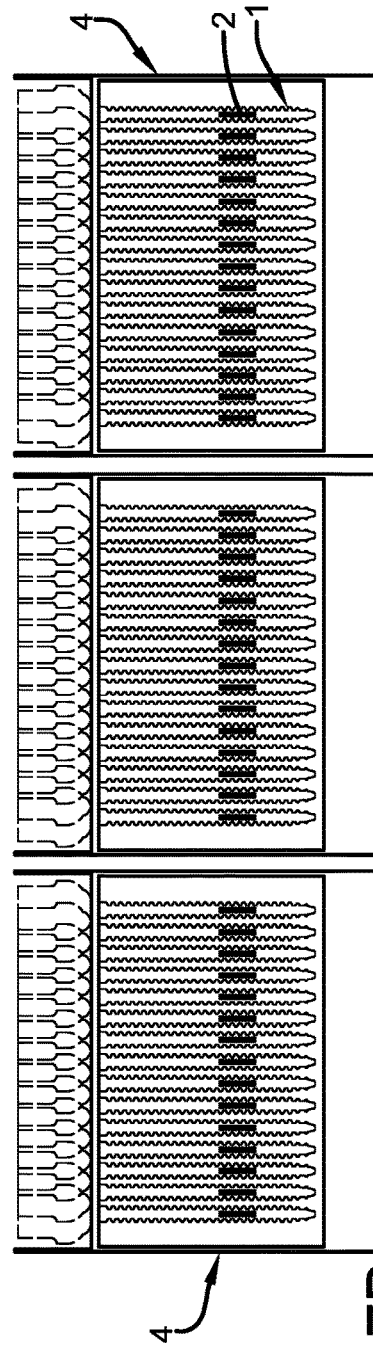
FIGURE 7A
FIGURE 7B

METHOD OF PRODUCING AN ELONGATE IMPLANT CONTAINING A STRUCTURALLY ENCODED PIN THROUGH ELECTRICAL DISCHARGE MACHINING

RELATED APPLICATION DATA

This application incorporates by reference all of the following in their entirety: (i) U.S. Provisional Application No. 61/938,475, filed Feb. 11, 2014; (ii) U.S. patent application Ser. Nos. 14/302,133, 14/302,171 (now U.S. Pat. No. 9,101,321) and 14/302,197, all filed Jun. 11, 2014; (iii) U.S. patent application Ser. No. 14/456,665, filed Aug. 11, 2014; (iv) U.S. Provisional Application No. 62/035,875, filed Aug. 11, 2014; (v) U.S. patent application Ser. No. 14/823,234, filed Aug. 11, 2015 (now U.S. Pat. No. 9,424,503); (vi) U.S. patent application Ser. No. 14/822,613, filed Aug. 10, 2015 (now U.S. Pat. No. 9,414,891); (vii) U.S. Provisional Application No. 62/204,233, filed Aug. 12, 2015; U.S. patent application Ser. No. 15/235,914, filed Aug. 12, 2016; (viii) U.S. Provisional Application No. 62/419,373, filed Nov. 8, 2016 and entitled Method of Producing Elongate Implant Containing A Structurally Encoded Pin Through Electrical Discharge Machining; (ix) U.S. Provisional Application No. 62/419,341, filed Nov. 8, 2016 entitled Elongate Implant Containing A Structurally Encoded Pin, Carrier And Reading System Therefor; and (x) U.S. Provisional Application No. 62/419,364, filed Nov. 8, 2016 entitled Optical Image Vertebral Implant Cage and Reading System Therefor. All of the forgoing are hereby incorporated by reference in their entirety.

CROSS-REFERENCE

This application claims priority from U.S. Provisional Application Nos. 62/419,364, 62/419,341, 62/419,353 and 62/419,373, all of which were filed on Nov. 8, 2016. This application is also a continuation in part of: (i) U.S. patent application Ser. No. 14/456,665, filed on Aug. 11, 2014, which claims priority to Provisional Patent Application Ser. No. 61/938,475 filed on Feb. 11, 2014; (ii) U.S. patent application Ser. No. 15/243,036, filed on Aug. 22, 2016, which is a continuation of U.S. patent application Ser. No. 14/823,234, filed on Aug. 11, 2015, (now U.S. Pat. No. 9,424,503), which claims the priority benefit of U.S. Provisional Application No. 62/035,875, filed Aug. 11, 2014; and (iii) U.S. patent application Ser. No. 15/403,063, filed on Jan. 10, 2017, which is a continuation of U.S. patent application Ser. No. 15/243,036, filed Aug. 22, 2016, which is a continuation of U.S. patent application Ser. No. 14/823, 234, filed on Aug. 11, 2015, (now U.S. Pat. No. 9,424,503), which claims the priority benefit of U.S. Provisional Application No. 62/035,875, filed Aug. 11, 2014.

FIELD OF THE INVENTION

The present invention relates to elongate implants containing a structurally encoded pin, a carrier and reading system therefor, as well as methods of identifying and encoding implants via an electric discharge machining process, and systems for identifying and encoding implanted devices.

BACKGROUND OF THE INVENTION

Medical implant devices used in surgical procedures can be associated with particular information to guide medical professionals before and after the surgical procedure. Each implant device carries a wealth of information that is valuable to the patient, the implant manufacturer, medical researchers, healthcare professionals, and medical facilities. However the information, which may include without limitation the implant manufacturer and manufacturer's lot number, the date and location of surgical implantation, the responsible surgeon, any medical notes, photographs, or diagrams relating to the implant, surgery, or condition, may not be adequate, properly recorded, or readily accessible for beneficial use by a healthcare professional, implant manufacturer, or medical researcher after implantation. Problems relating to poor implant records can lead to unnecessary delay or even medical error by healthcare professionals. Moreover, there are many different implant identification methods currently in place instead of a common system to allow manufacturers, distributors, and healthcare facilities and professionals to effectively track, identify, and manage implant devices and medical device recalls. The U.S. Food and Drug Administration recently announced a program focusing on requirements for unique device identifiers for every medical implant device to address the need for a more robust implant device identification system, the details of which are incorporated by reference herein: www.fda.gov/udi as of the filing date.

In the use of elongate implants it is also beneficial to provide means for organizing, reading, inventorying, and using such implants in a therapeutic application, such as in surgical settings and the like. Consequently, there is a long felt need in the art for an implant device that enables a provider to quickly and un-invasively retrieve information from said implanted device, post implantation. There is also a long felt need for a structurally encoded implant device, such as a pin that protects patient privacy. Finally, there is a long felt need for a structurally encoded implantable device that accomplishes all of the forgoing objectives, and that is relatively inexpensive to manufacture and safe and easy to use.

SUMMARY OF THE INVENTION

The following presents a simplified summary in order to provide a basic understanding of some aspects of the disclosed invention. This summary is not an extensive overview, and it is not intended to identify key/critical elements or delineate the scope thereof. Its sole purpose is to present some concepts in a simplified form as a prelude to the more detailed description later.

In accordance with an aspect of the invention, the present invention comprises an elongate implant containing a structurally encoded pin, such as a functional screw bearing an encoded, longitudinally-extending radiopaque insert. This aspect of the invention includes an elongate implant containing a structurally encoded insert comprising: an implant body defining a longitudinal axis; and a structurally encoded pin contained within the implant body and aligned substantially along the longitudinal axis, the structurally encoded pin comprising a shape or surface characteristics discernable by an imaging modality such as, but not limited to, x-ray, fluoroscopy, computed tomography, electromagnetic radiation, ultrasound, and magnetic resonance imaging from outside the screw body, the shape or surface characteristics representing structurally encoded data. The readable portion of the encoded pin may further comprise a radiopaque insert and indicia disposed along at least one surface thereof or disposed within the implant. The indicia may comprise a plurality of modifications to at least one surface of the radiopaque element or a plurality of radiopaque elements disposed within the readable portion such that the indicia are discernible by any imaging modality such as x-ray, fluoroscopy, computed tomography, electromagnetic radiation, ultrasound, visible light, UV light, fluoroscopy, electromagnetic radiation, and magnetic resonance imaging. The plurality of modifications may comprise an array of holes and/or notches in the at least one surface of the radiopaque element. The plurality of modifications may comprise an array of notches in the at least one surface of the radiopaque element. The array of notches in the at least one surface of the radiopaque element may form at least one bar code. The at least one bar code may comprise a Hamming or similar type of code.

The elongate implant may be any implant amenable to the inclusion of an encoded, longitudinally extending radiopaque insert (i.e., relatively radiopaque with respect to that of the implant material) and may include pedicle screws, surgical rods, pins, stents and the like. In one embodiment, the elongate implant (such as a pedicle screw) may be cannulated and the structurally encoded pin likewise cannulated so that the elongate implant may accept the encoded pin and also be amenable for use in a minimal invasive surgical (MIS) operation. Accordingly, the structurally encoded pin contained therein may itself be cannulated so as to be able, when disposed within the elongate implant and aligned along the desired cannula axis, accept a guide wire. As such, the resultant cannulated elongate implant presents a channel through both the structurally encoded pin and the elongate implant so as to be able to be borne on an insertion wire used in such procedures. The present invention thus includes an embodiment wherein the implant body comprises an implant body longitudinal cannula extending through the implant body. Additionally, the structurally encoded pin may be contained within the implant body longitudinal cannula, with the structurally encoded pin itself comprising a pin longitudinal cannula, with the implant body longitudinal cannula and pin longitudinal cannula being aligned so as to create a wire-accepting cannula there through.

Alternatively, the present invention may include an elongate implant comprising: an implant body defining a longitudinal axis; and a structurally encoded pin contained within the implant body and aligned substantially along the longitudinal axis, the structurally encoded pin comprising a shape or a surface characteristics discernable by an imaging modality such as, but not limited to, x-ray, fluoroscopy, computed tomography, electromagnetic radiation, ultrasound, visible light, UV light, magnetic resonance imaging, positron emission tomography and neutron imaging, from outside the screw body, the shape or surface characteristics representing structurally encoded data. The shape or surface characteristics may be placed in the structurally encoded pin through electronic discharge manufacturing or through additive manufacture.

The elongate implant may serve as any bodily implant or part thereof, such as articles selected from the group consisting of pedicle screws, rods and surgical pins. In some implants the implant body comprises an implant body longitudinal cannula extending through the implant body, and may be such that the structurally encoded pin is contained within the implant body longitudinal cannula. The structurally encoded pin comprises a pin longitudinal cannula, and the implant body longitudinal cannula and the pin longitudinal cannula are aligned with one another.

The present invention also includes a method of producing an elongate implant containing a structurally encoded pin and comprising: preparing a readable encoded relatively radio-opaque insert portion of the implant, the insert portion encoded with data relating to the implant and encoded into the insert portion through an electronic discharge manufacturing or additive manufacturing process; and encasing or inserting the insert portion into the elongate implant so as to contain the insert portion therein.

Additionally, the implant body may be manufactured so that there is an implant body longitudinal cannula extending through the implant body, and wherein the structurally encoded pin is contained within the implant body longitudinal cannula, and further wherein the structurally encoded pin is formed to include a pin longitudinal cannula, the implant body longitudinal cannula and the pin longitudinal cannula being aligned once encased or inserted into the elongate implant.

The present invention may also include an array of elongate implants (such as functional screws, pins, rods, stents and the like) bearing an encoded, longitudinally-extending radiopaque insert, the array being disposed in a non-eclipsed array with respect to a source of reading illumination of any imaging modality.

Another aspect of the present invention is a carrier containment system adapted to contain a plurality of elongate implants (such as functional screws, pins, rods, stents and the like) bearing an encoded, longitudinally-extending radiopaque insert, and to maintain the plurality of functional implants in an array, the array being disposed in a non-eclipsed disposition with respect to the source of illumination, and amenable to sterilization. The carrier may be made of any appropriately radio-translucent material to permit imaging of the encoded inserts, and to permit sterilization where desired, such as plastic materials.

Yet another aspect of the present invention is a method of reading, from a single vector, data from a plurality of elongate implants (such as functional screws, pins, stents and the like) bearing an encoded, longitudinally-extending radiopaque insert, and arranged in an array, the array being disposed such that the inserts are maintained in a non-eclipsed disposition with respect to the source of illumination. The method also includes steps of decoding the data, storing the data for retrieval, and/or displaying information associated with the implant based on the indicia and the plurality of records through a user interface, in accordance with known data processing and computer displays currently being used in the art.

In accordance with further aspects of the present invention, a method of manufacturing an elongate implant bearing the relatively radio-opaque insert is provided. This method comprises generally preparing a readable encoded relatively radio-opaque insert portion of the implant, and inserting or otherwise manufacturing through a co-injection molding, additive manufacturing or other suitable manufacturing process, a main portion of the implant device so as to contain the readable insert portion of the implant. This may be done by 3D printing a first relatively radio-opaque material so as to structurally encode the predetermined data into the readable insert portion surface, and further 3D printing the second implant body material onto the first readable insert portion to enclose it within the implant body material. This also may be done by equivalent molding methods effective to enclose the readable insert portion within the implant body material. As an alternative, the implant body material may be manufactured first, followed by drilling a channel into which the readable insert portion may be inserted and the channel closed thereafter in a secondary molding or additive manufacture operation.

The material from which the relatively radio-opaque insert may be produced, especially through additive manufacture, may be selected from the group consisting of relatively radio-opaque polymers, ceramics, rubbers, metals, alloys or mixture thereof, using the additive manufacture processes and devices known and used in the art to create such objects. Other materials may include relatively radio-opaque hydrogels, fluids, biologic materials, and the like that may be adapted to be structurally encoded so as to maintain a shape encoding data as described herein.

Another aspect of the present invention comprises a method machining of notches in implants such as pins through electrical discharge machining (EDM) processes to produce arrays of wires or sinkers. These arrays may then be linked to software controlling the encoded patterns representing data such as sequential serial numbers so parts could automatically be made without operator interaction. EDM applicable to the invention may create a desired shape by using electrical discharges to remove material from the workpiece by a series of rapidly recurring current discharges between two electrodes, separated by a dielectric liquid and subject to an electric voltage. This method thus affords a relatively inexpensive and efficient process by way of which encoded data may be embodied in the elongate implant.

The present invention further comprises a reading system for reading a plurality of elongate implants each containing a structurally encoded pin, comprising: a carrier having a front surface defining a front axis and an upper surface, the upper surface having a plurality of apertures arrayed in one or more series at an angle to the front axis, such that all the elongate implants extending through each of the apertures in the series may be read by a source of reading illumination directed along a vector approximately orthogonal to the front axis; a plurality of elongate implants extending through each of the apertures in the series, each elongate implant defining a longitudinal axis, and having a structurally encoded pin contained within the elongate implant and aligned substantially along the longitudinal axis, the structurally encoded pin having a shape or surface characteristics discernable by the source of reading illumination from outside the elongate implant, the shape or surface characteristics representing structurally encoded data; and a source of reading illumination directed at the plurality of elongate implants along the vector orthogonal to the front axis.

The source of reading illumination may be selected from the group consisting of x-ray, fluoroscopy, computed tomography, electromagnetic radiation, ultrasound, visible light, UV light, magnetic resonance imaging, positron emission tomography and neutron imaging.

The reading system may also optionally include means of moving the source of reading illumination with respect to the carrier along the front axis. This means may include any means such as manual movement or through the use of mechanical or electromechanical arrangements adapted to move the reading illumination with respect to the carrier along the front axis, such as along the axes described in the drawings.

Also included in the present invention is a method of reading a plurality of elongate implants each containing a structurally encoded pin, comprising: providing a carrier having a front surface defining a front axis and an upper surface, the upper surface having a plurality of apertures arrayed in one or more series at an angle to the front axis, such that all the elongate implants extending through each of the apertures in the series may be read by a source of reading illumination directed along a vector orthogonal to the front axis; the carrier containing a plurality of elongate implants extending through each of the apertures in the series, each elongate implant defining a longitudinal axis, and having a structurally encoded pin contained within the elongate implant and aligned substantially along the longitudinal axis, the structurally encoded pin having a shape or surface characteristics discernable by the source of reading illumination from outside the elongate implant, the shape or surface characteristics representing structurally encoded data; and positioning the source of reading illumination directed at the plurality of elongate implants along the vector orthogonal to the front axis, so as to read the structurally encoded data from each of the elongate implants. This method may additionally comprise the step of decoding the structurally encoded data through microprocessor driven algorithms, and/or storing the structurally encoded data using computer and electronic storage media, and the like.

The present invention further comprises a reading system for reading a plurality of implants (such as those of shapes other than those that lend themselves to being held by a carrier of the type described for elongate implants), each containing a relatively radiopaque encoded portion. This system comprises: a carrier having a front surface defining a front axis and an upper surface, the upper surface comprising a plurality of wells arrayed in one or more series at an angle to the front axis, such that all the radiopaque encoded portions, when the implants are contained within the wells may be read by a source of reading illumination directed along a vector orthogonal to the front axis; a plurality of implants each containing a relatively radiopaque encoded portion and contained within the wells in the one or more series, each the radiopaque encoded portion having a shape or surface characteristics discernable by the source of reading illumination from outside the implant, the shape or a plurality of surface characteristics representing structurally encoded data; and a source of reading illumination directed at the plurality of implants along the vector orthogonal to the front axis.

The source of reading illumination and means of moving the source of reading illumination with respect to the carrier along the front axis may be as described supra.

Also included in the present invention is a method of reading a plurality of implants each containing a relatively radiopaque encoded portion, comprising: providing a carrier having a front surface defining a front axis and an upper surface, the upper surface having a plurality of wells arrayed in one or more series at an angle to the front axis, such that all the radiopaque encoded portions, when the implants are contained within the wells may be read by a source of reading illumination directed along a vector orthogonal to the front axis the carrier containing a plurality of implants each containing a relatively radiopaque encoded portion and contained within the wells in the one or more series, each the radiopaque encoded portion having a shape or surface characteristics discernable by the source of reading illumination from outside the implant, the shape or surface characteristics representing structurally encoded data; and directing an external source of reading illumination at the plurality of elongate implants along the vector orthogonal to the front axis, so as to read the structurally encoded data from each of the elongate implants. This method may further comprise the additional steps of decoding the structurally encoded data through microprocessor driven algorithms, and/or storing the structurally encoded data using computer and electronic storage media, and the like.

Accordingly, the implants of the present invention may have encoded therein some information through the use of the structurally encoded pins of the present invention, while other information may be encoded through use of the encoded inclusion patterns described in the referenced application. Likewise, by combining aspects of the invention one can use the methods together for similar information (either for redundancy or using different methods for reading the information), different information, or some combination of the same or different information, as well as further through the use of embedded chips, etc. for other information within such an encoding scheme.

It will be appreciated that the present invention may be applied to other fields for the inventory management of articles in any industry, such as in the case of articles that may include parts used in manufacturing, such as in the case of automobiles and parts therefor, firearms and parts therefor or jewelry and parts therefor.

In the use of elongate implants it is also beneficial to provide means for organizing, reading, inventorying and using such implants in a therapeutic application, such as in surgical settings and the like.

The container of the present invention may be used along with a source of reading illumination, such as x-rays and the like, so as to permit all of the encode inserts in respective articles to be viewed (and decoded) to permit inventory to be tracked and managed in the same manner as the subject implants may be tracked and managed both before and after introduction into the body. The present invention may be applied to other industries, allowing the operator to track anything in any industry with an encoded insert or pin and a source of reading illumination, such as x-rays or the like.

To the accomplishment of the forgoing and related ends, certain illustrative aspects are described herein in connection with the following description and the annexed drawings. These aspects are indicative of the various ways in which the principles disclosed herein can be practiced and all aspects and equivalents thereof are intended to be within the scope of the claimed subject matter. Other advantages and novel features will become apparent from the detailed description when considered in conjunction with the drawings.

BRIEF DESCRIPTION OF THE DRAWINGS

While the specification concludes with claims particularly pointing out and distinctly claiming the present invention, it is believed that the present invention will be better understood from the following description in conjunction with the accompanying Figures, in which like reference numerals identify like elements, and wherein:

FIG. 7A illustrates a mock x-ray image of an elevation view of the carrier bearing the plurality of elongate implants in accordance with the disclosed architecture.

FIG. 7B illustrates a mock x-ray image of an elevation view of the container bearing three carriers in turn each carrier bearing some of the plurality of elongate implants in accordance with the disclosed architecture.

DETAILED DESCRIPTION

In the following detailed description of the preferred embodiment, reference is made to the accompanying drawings that form a part hereof, and in which is shown by way of illustration, and not by way of limitation, a specific preferred embodiment in which the invention may be practiced. It is to be understood that other embodiments may be utilized and that changes may be made without departing from the spirit and scope of the present invention.

The invention generally relates to an elongate implant comprising an implant body defining a longitudinal axis; and a structurally encoded pin contained within the implant body and aligned substantially along the longitudinal axis, the structurally encoded pin comprising a shape or a plurality of surface characteristics representing structurally encoded data which may be discerned from outside the implant body via a variety of imaging modalities, a carrier for the same, and systems and methods of using both.

Figure 1:
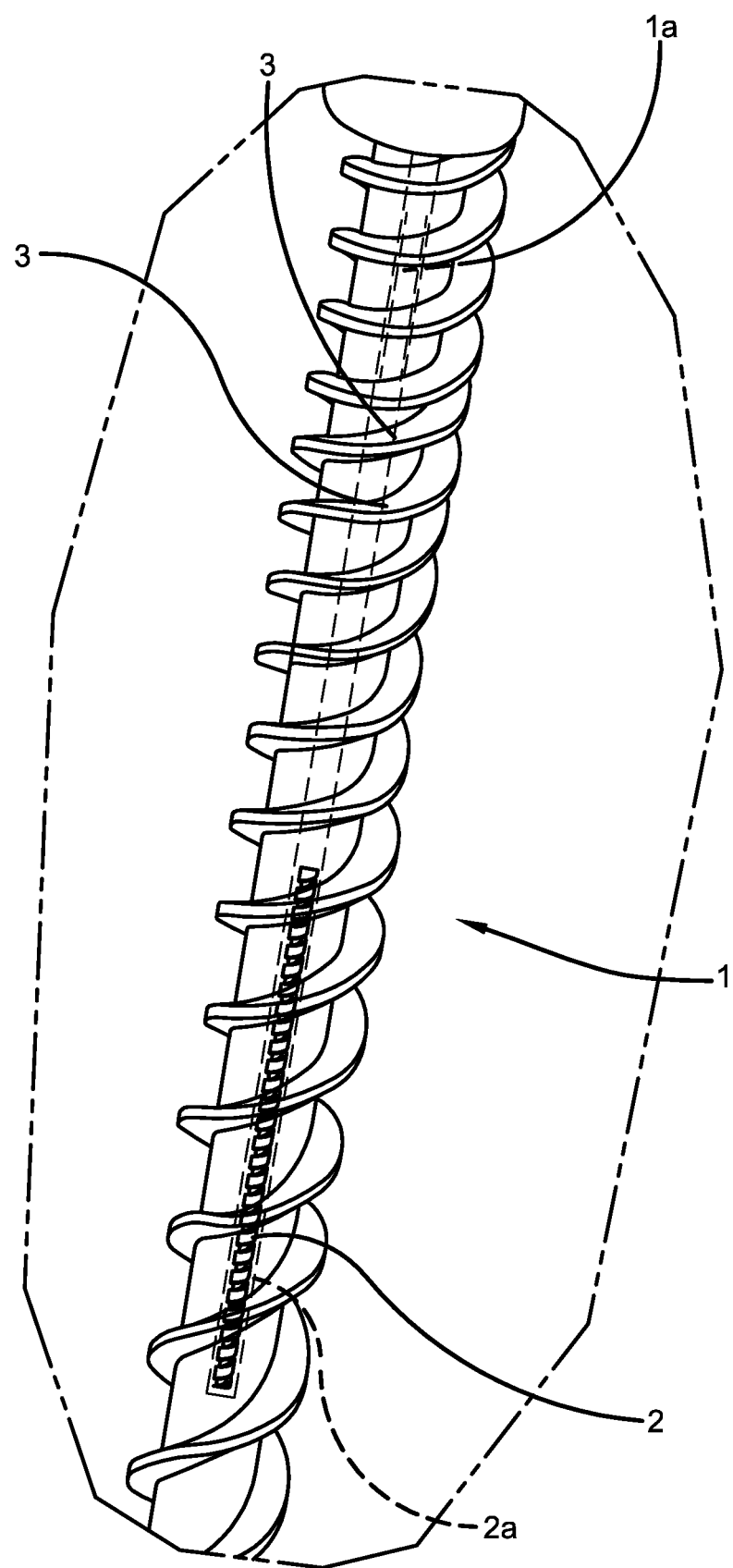
FIG. 1 illustrates an in situ view of an x-ray image of an elongate implant in accordance with the disclosed architecture.

FIG. 1 illustrates an in situ view of an x-ray image of an elongate implant 1, such as, but not limited to a relatively radio-translucent pedicle screw visible via an imaging modality 10, such as an x-ray. The elongate implant 1 comprises an implant body (represented by the screw body) having a longitudinal axis and a structurally encoded pin 2. The structurally encoded pin 2 is relatively radio-opaque and can be clearly seen and generally appears as greyish-black in color in an x-ray as illustrated. The elongate implant 1 may comprise a plurality of male threads 3 which can also be seen as greyish in color and relatively less opacity on an x-ray.

The elongate implant 1 (such as a pedicle screw, rod or surgical pin) may be cannulated and comprise a longitudinal cannula 1A, such as a channel within the implant body, with the structurally encoded pin 2 astride the longitudinal cannula 1A. The structurally encoded pin 2 (i.e., radio-opaque encoded pin) likewise may comprise a longitudinal cannula 2A aligned the longitudinal channel 1A of the elongate implant 1 so that the elongate implant 1 may accept the structurally encoded pin 2 within and also be amenable for use in a minimal invasive surgical (MIS) operation. Accordingly, the structurally encoded pin 2 contained therein may itself be cannulated so that, when disposed or contained within the elongate implant 1 and aligned along the desired cannula axis, the resultant cannulated elongate implant 1 presents a channel (1A and 2A collectively) through both the structurally encoded pin 2 and the elongate implant 1 so that the elongate implant 1 may be borne on an insertion wire used in such procedures.

This encoder-pin variant of the present invention not only works for the elongate implant 1 comprising a single pedicle screw, but also works on a group of devices such as a plurality of pedicle screws resting inside a caddy/tray. The advantage is that a health care provider may image an entire set of implants or interbody devices, and decode the structurally encoded information for full implant and instrument traceability. In order to do this, the carrier or caddy should feature holes orientated such as those shown in FIGS. 2 and 3 based on the size and geometry of the pedicle screws, such that when x-ray or other reading radiation is emitted from the side direction, the implants or interbody devices, such as pedicle screws, will not overlap with each other and result in eclipsed or otherwise unclear images.

Figure 4:
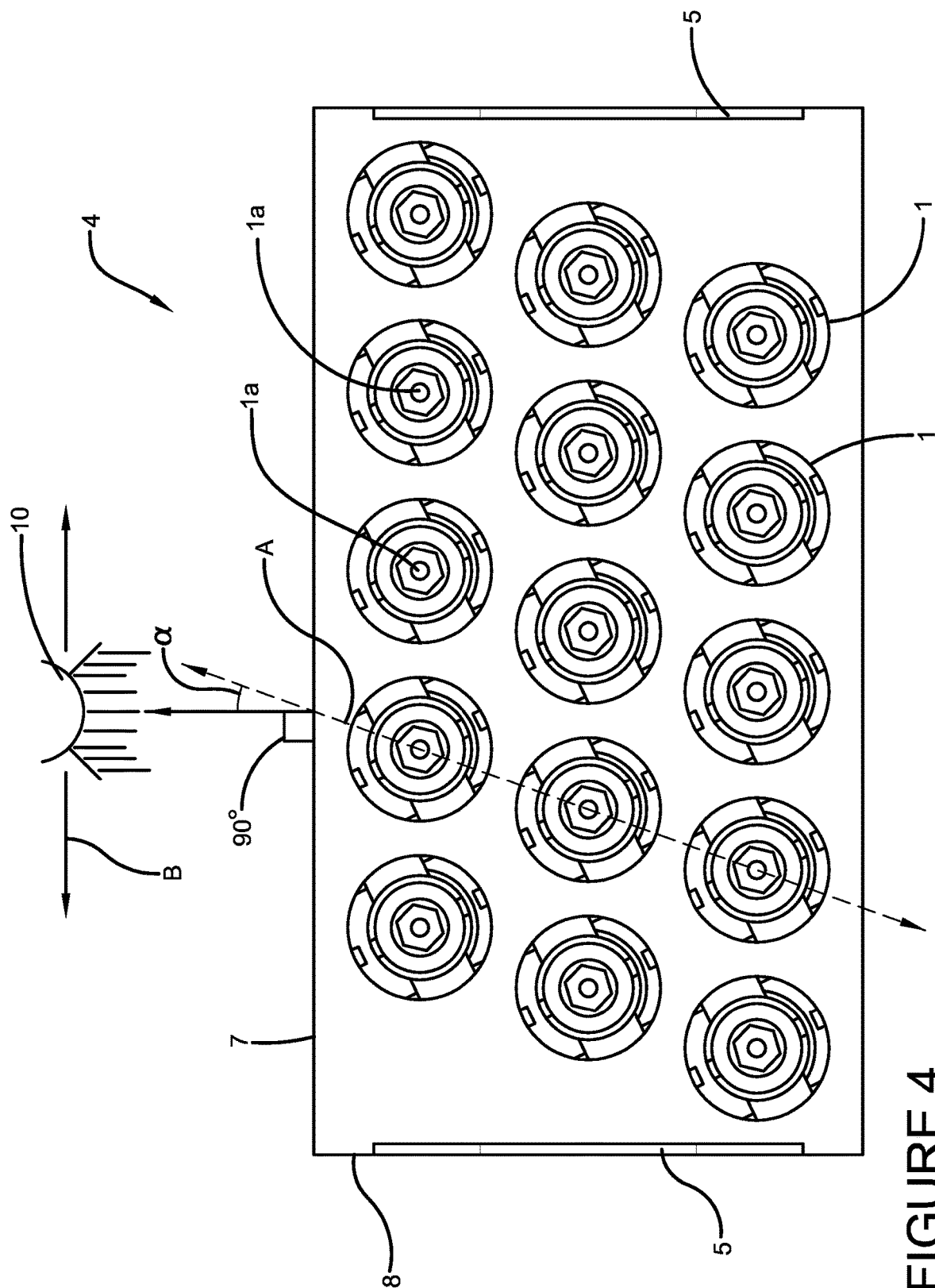
FIG. 4 illustrates a top plan view of the carrier bearing the plurality of elongate implants in accordance with the disclosed architecture.

The structurally encoded pin 2 used with the elongate implant 1, or any interbody device as described infra, comprises a shape or a plurality of surface characteristics to represent structurally encoded data. While the shape is illustrated in FIGS. 1 and 4 as a rod or pin shape, as a disc shape in FIGS. 10 and 11, and geometrically shaped in FIGS. 12-14, the implant may comprise any shape desirable for an implantable device. One example of the plurality of surface characteristics may be the notches illustrated in FIG. 15 as described infra.

Figure 2:
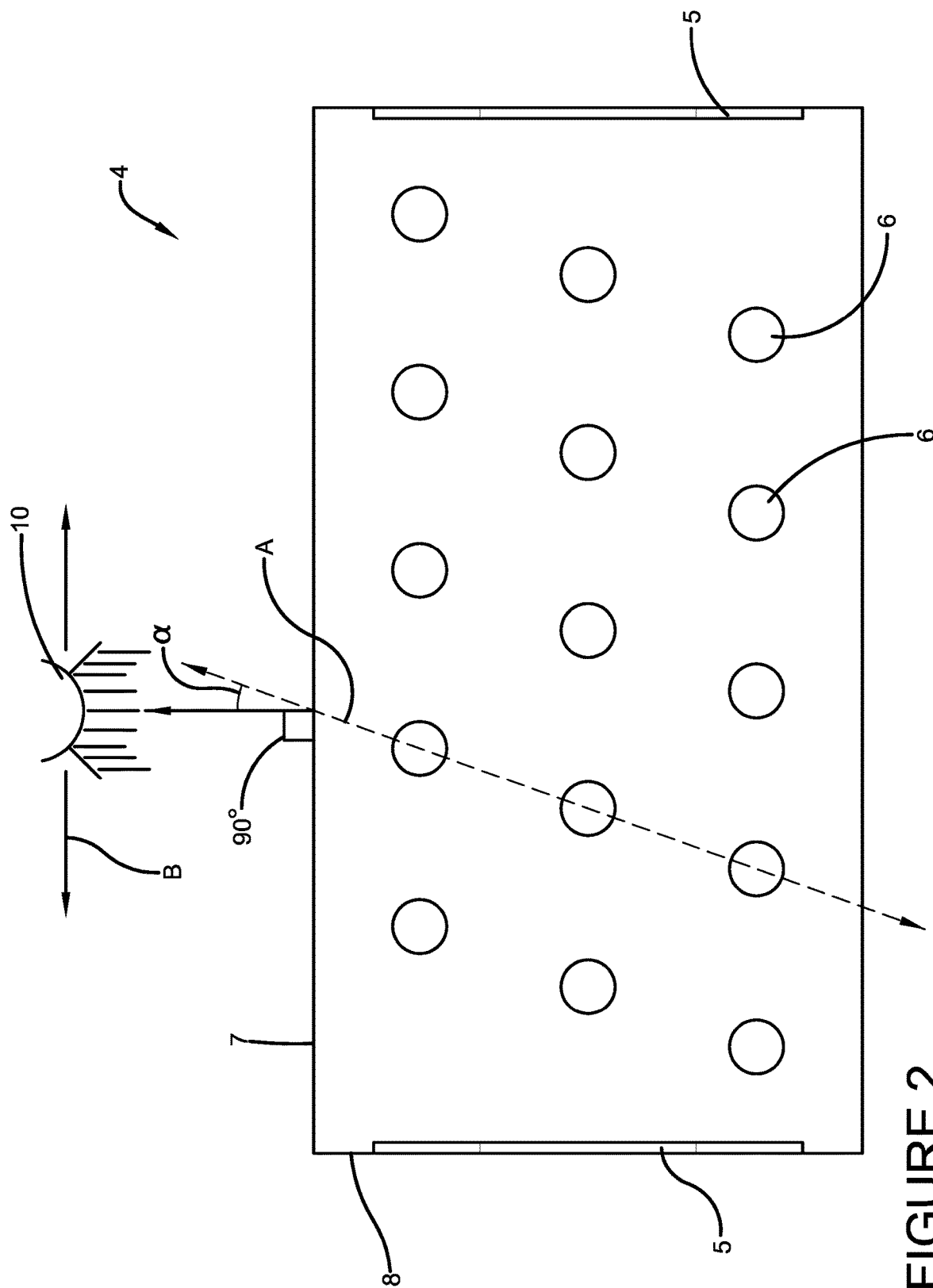
FIG. 2 illustrates a top plan view of a carrier for retaining a plurality of elongate implants in accordance with the disclosed architecture.

FIG. 2 illustrates a top plan view of a carrier 4, such as, but not limited to, a pedicle screw carrier in accordance with further aspects of the present invention. The carrier 4 may comprise a plurality of handles 5 and a plurality of holding apertures 6 located in an upper surface of the carrier 4 that are sized so as to be able to accept a series of elongate implants 1 as shown in more detail in FIGS. 4 and 5.

Figure 3:
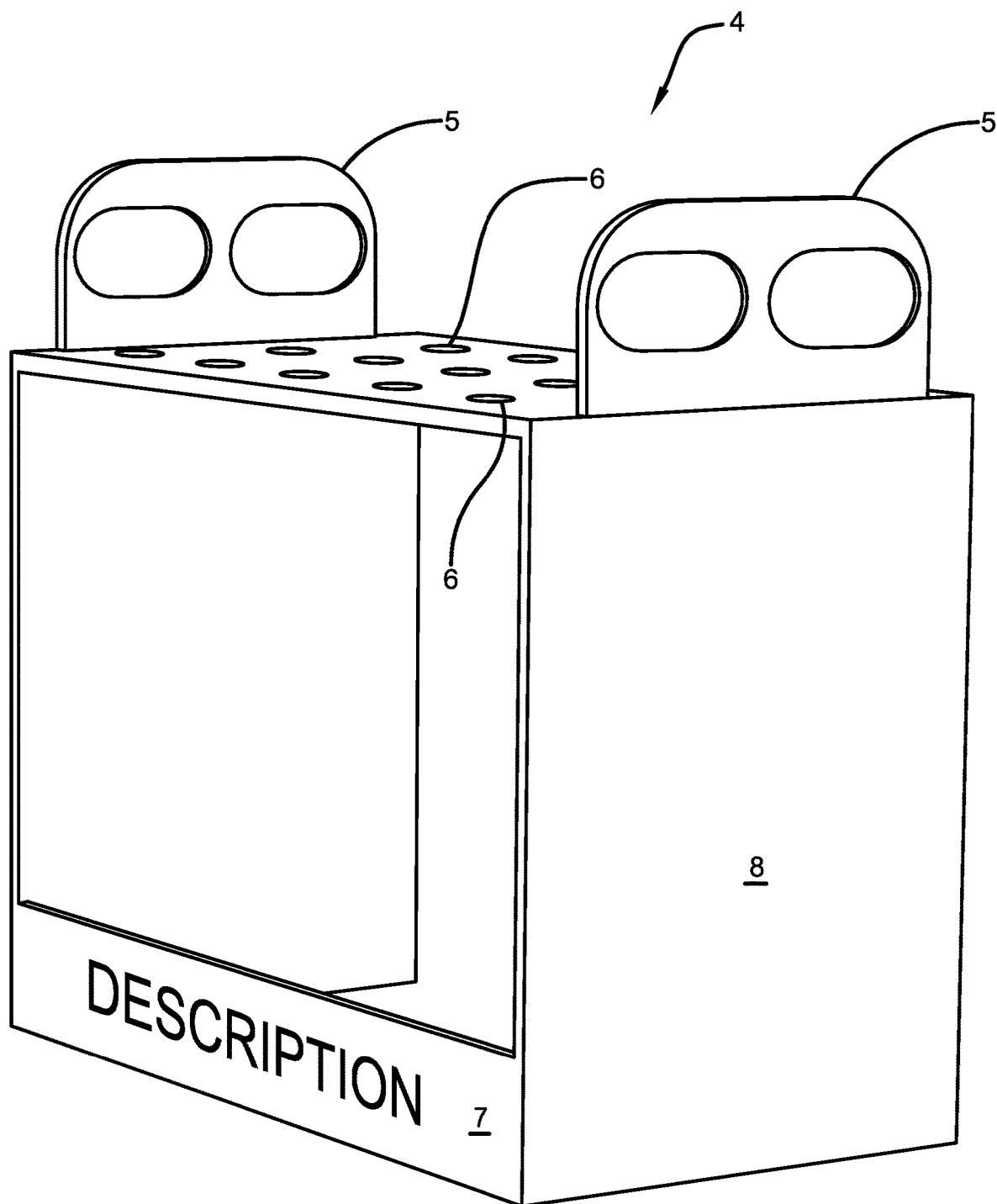
FIG. 3 illustrates a front perspective view of the carrier in accordance with the disclosed architecture.

FIG. 3 is a front perspective view of the carrier 4 empty of any elongate implants 1. The carrier 4 comprises a front surface 7 and a side surface 8. The plurality of holding apertures 6 are preferably arrayed in one or more series at an angle to the front 7 or side surface 8, such as arrayed along axis A at an acute angle alpha with respect to front surface 7, so as to allow the carrier 4 to be placed against an alignment surface or device (not shown), so as to permit the user to scan the population of contained elongate implants 1 with the source of reading illumination 10. The source of reading illumination 10 may be moved along or reciprocated along direction B, such that the plurality of structurally encoded pins 2 may be conveniently read without some of the pins eclipsing and thus obscuring other pins in the array. The imaging modality 10 may comprise x-ray, fluoroscopy, computed tomography, electromagnetic radiation, ultrasound, visible light, UV light, magnetic resonance imaging, positron emission tomography and neutron imaging, and the like.

Figure 6:
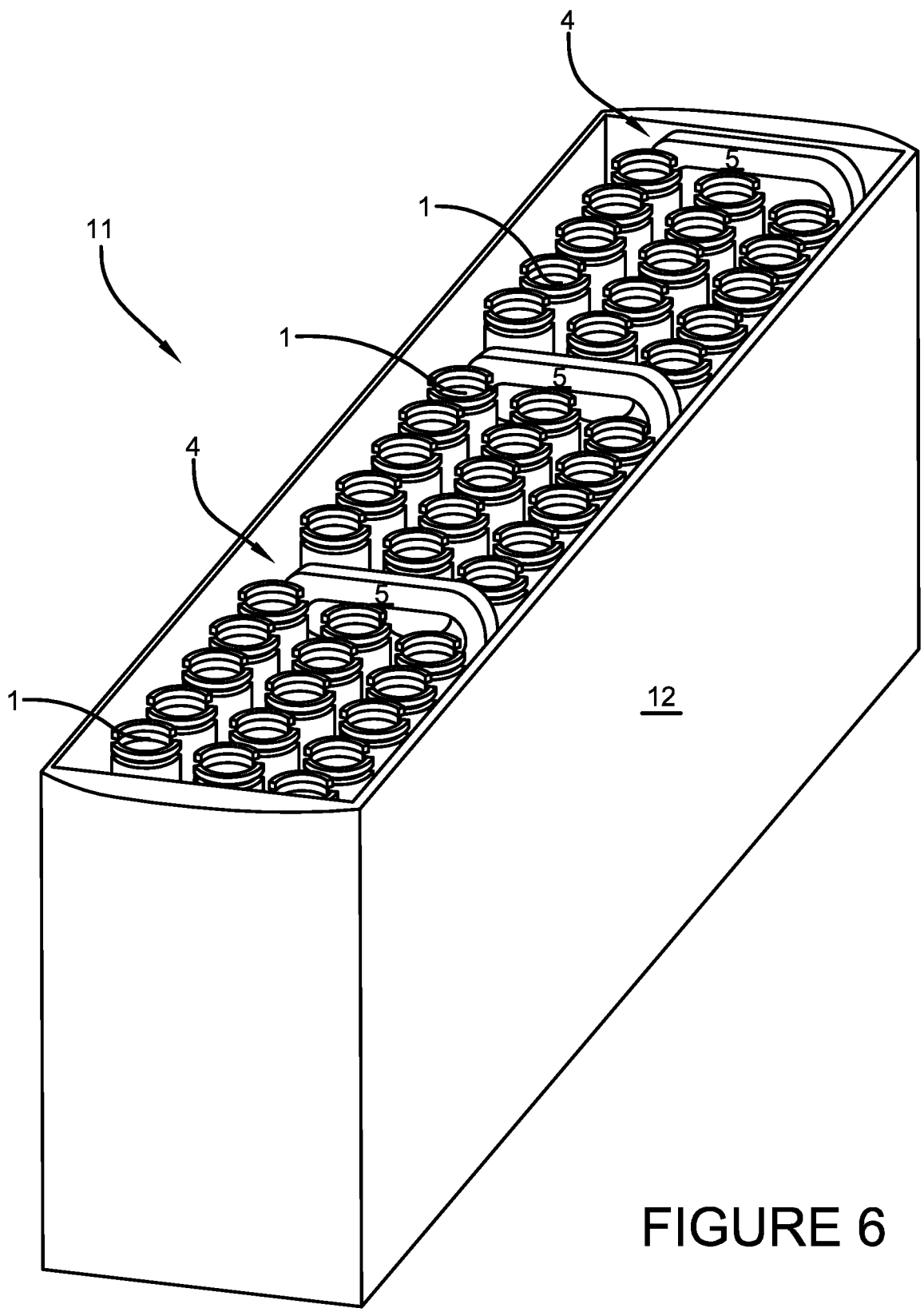
FIG. 6 illustrates an upper perspective view of a container bearing three carriers in turn each carrier bearing some of the plurality of elongate implants in accordance with the disclosed architecture.

The alignment surface or device may be in the form of an interior surface of container 11 shown in FIG. 6, or that of a tray or even a surface associated with the illumination device itself, to provide alignment, typically orthogonal alignment, to the reading illumination direction.

FIG. 4 is a top plan view of the carrier 4 bearing the plurality of elongate implants 1 extending through the plurality of holding apertures 6 so as to extend below the aperture-containing top surface of the carrier 4 and generally into free space within the carrier interior to permit the threaded portion 3 of each elongate implant 1 to be substantially unobscured by any portion of the carrier 4 when read from a direction substantially orthogonal to the front surface 7, as may be appreciated from FIG. 5. FIG. 4 also shows the position of the longitudinal cannula 1A in each of the elongate implants 1 as an optional feature shown and described in FIG. 1. When disposed within the elongate implant 1 and aligned along the desired longitudinal cannula axis, the longitudinal cannula 1A of the elongate implant 1 and the longitudinal cannula 2A within the structurally encoded pin 2 create a channel (1A and 2A collectively) through both the structurally encoded pin 2 and the elongate implant 1 so as to be able to be borne on an insertion wire used in such procedures.

Figure 5:
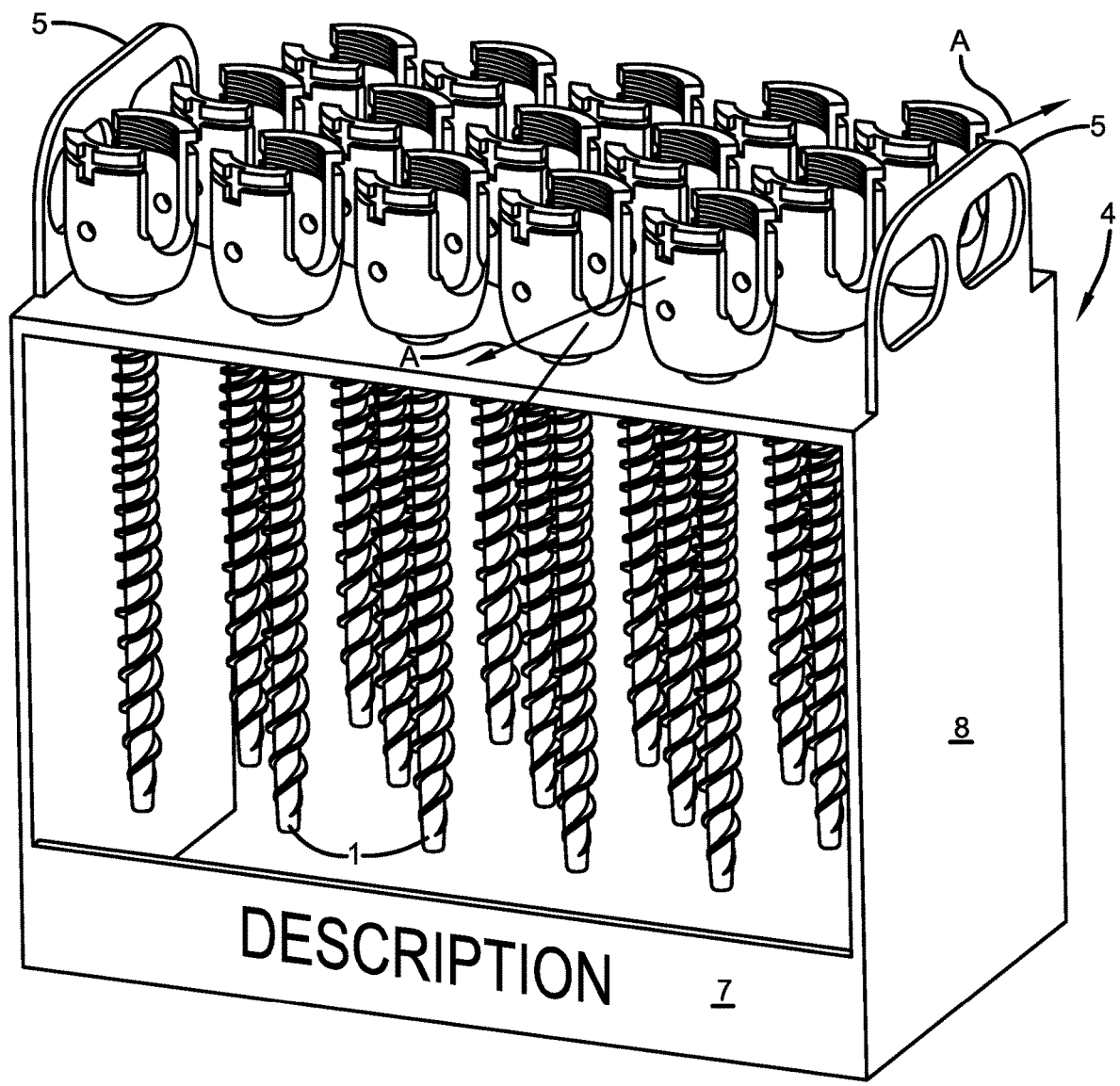
FIG. 5 illustrates a front perspective view of the carrier bearing the plurality of elongate implants in accordance with the disclosed architecture.

It will also be appreciated from FIG. 5 that an array of the holding apertures 6 will also be dependent upon the size and geometry of the elongate implants 1, such that when X-ray is emitted from source 10, the elongate implants 1 will not eclipse one another, resulting in unclear images and potential attendant misreading of the encoded structure of the structurally encoded pins 2.

FIG. 6 shows a container 11 that may be used for storage or as an imaging caddy for the implants or interbody devices of the present invention. As such, the carrier 4 or a plurality of carriers is retainable by within the container 11. FIG. 6 shows the elongate implants 1, such as pedicle screws, placed and resting within a plurality of the carriers 4 (as seen more clearly in FIGS. 4 and 5). Three carriers 4 are shown as are placed inside one container 11.

The elongate implants 1 or interbody devices can be stored and sterilized in several ways in which the structurally encoded pins 2 may be viewed from X-ray images thereof. FIG. 6 illustrates an upper perspective view of the container 11 bearing three carriers 4 as shown in FIGS. 4 and 5. The container 11 aligns the respective front (open) sides (i.e., the front surface 7 of each carrier 4) and may in turn be used to align those exposed sides, and the elongate implants 1 they expose, with respect to the reading illumination source 10, such as by having a longitudinal side 12 of the container 11 juxtaposed against a bearing surface (not shown) that aligns the container 11 approximately orthogonally with respect to the reading illumination source 10.

FIG. 7A illustrates a mock x-ray image of an elevation view of the carrier 4 representing a single surgical pedicle screw carrier bearing the plurality of pedicle screws 1, and FIG. 7B illustrates a mock x-ray image of an elevational view of three carriers 4 each bearing pedicle screws within a container (not shown) that is not visible via an x-ray, and showing the respective position of the contained radio-opaque structurally encoded pins 2 in accordance with further aspects of the present invention. FIGS. 7A and 7B show the structurally encoded pins 2 clearly and unobstructed visible along with the caddy description underneath. The caddy description represented by the word DESCRIPTION on the side of the front surface 7 may be readable both with and without x-ray for further clarification to the user. The structurally encoded pins 2 are clearly visible along with the caddy description beneath them in the depicted embodiment. The advantage is that a health care provider may image an entire set and decode for full implant and instrument traceability.

Figure 8:
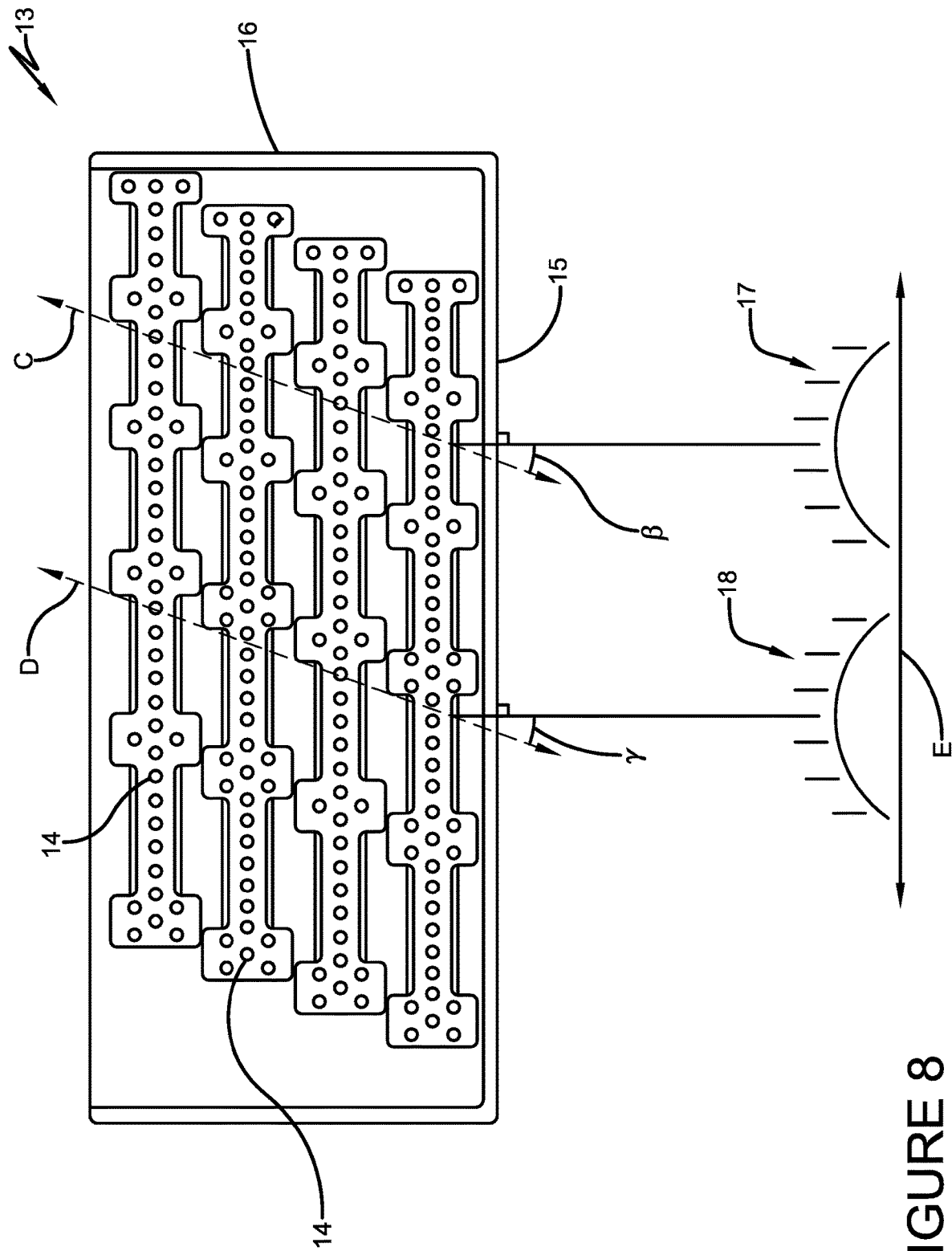
FIG. 8 illustrates a top plan view of an empty interbody cage carrier in accordance with the disclosed architecture.

FIG. 8 is a top plan view of an empty interbody cage carrier 13 in accordance with another embodiment of the present invention. The interbody cage carrier 13 is shown without handles though they may be provided as in the carrier 4 if desired. The interbody cage carrier 13 comprises a plurality of holding apertures 14 that are sized so as to be able to accept a series of interbody cages or carriers 4 similar to the manner as shown in FIGS. 4 and 5. The plurality of holding apertures 14 are preferably arrayed in one or more series at an angle to a front surface 15 or a side surface 16 (such as arrayed along axis C or D at acute angles beta or gamma respectively with respect to the front surface 15) so as to allow the interbody cage carrier 13 to be placed against an alignment surface or device so as to permit the user to scan the population of contained interbody cages or carriers 4 with a plurality of sources of reading illumination 17 and 18 that may be moved along or reciprocated along direct E. Thus, any radio-opaque encoded pins, such as the structurally encoded pins 2 of the plurality of elongate implants 1 (not shown), may be conveniently read without some of the pins eclipsing and thus obscuring other pins in the array. The plurality of sources of reading illumination 17 and 18 comprise imaging modalities such as x-ray, fluoroscopy, computed tomography, electromagnetic radiation, ultrasound, visible light, UV light, magnetic resonance imaging, positron emission tomography and neutron imaging, and the like as described supra.

Figure 9:
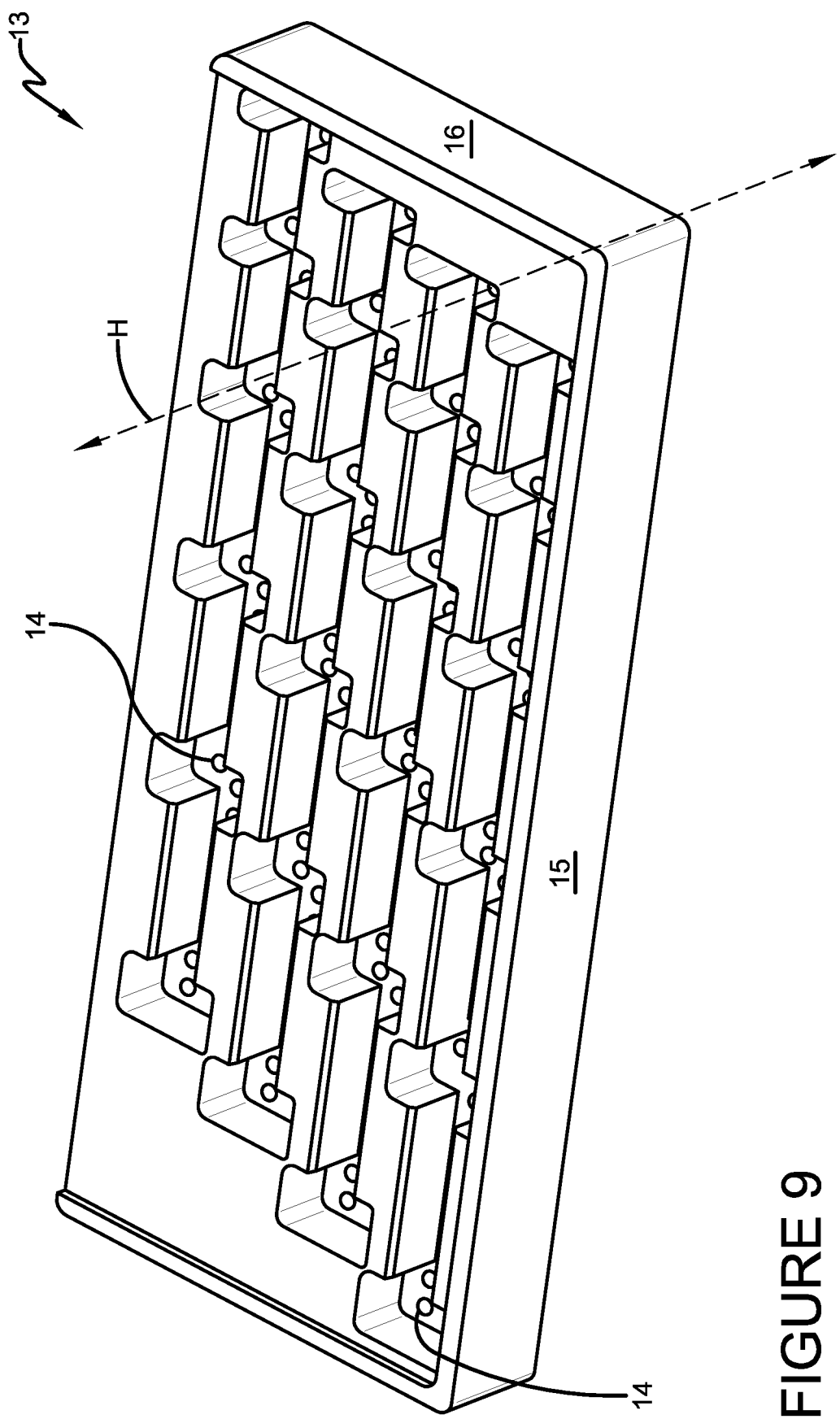
FIG. 9 illustrates a top perspective view of the empty interbody cage carrier in accordance with the disclosed architecture.

FIG. 9 illustrates a top perspective view of the empty interbody cage carrier 13. In this illustration, the carriers 4 or interbody cages may be inserted into the interbody cage carrier 13 so as to extend along line H below a bottom of the interbody cage carrier 13 and into an intended path of the sources of reading illumination 17 and 18. The interbody cage carrier 13 may be used in conjunction with an additional tray or similar container having a top edge that is sized to engage the interbody cage carrier 13 so as to permit the interbody cages to be secured in an enclosed space to maintain sterility. FIGS. 8 and 9 thus show unloaded versions of the interbody cage carrier 13 further depicted and described in FIGS. 13 and 14.

Figure 10:
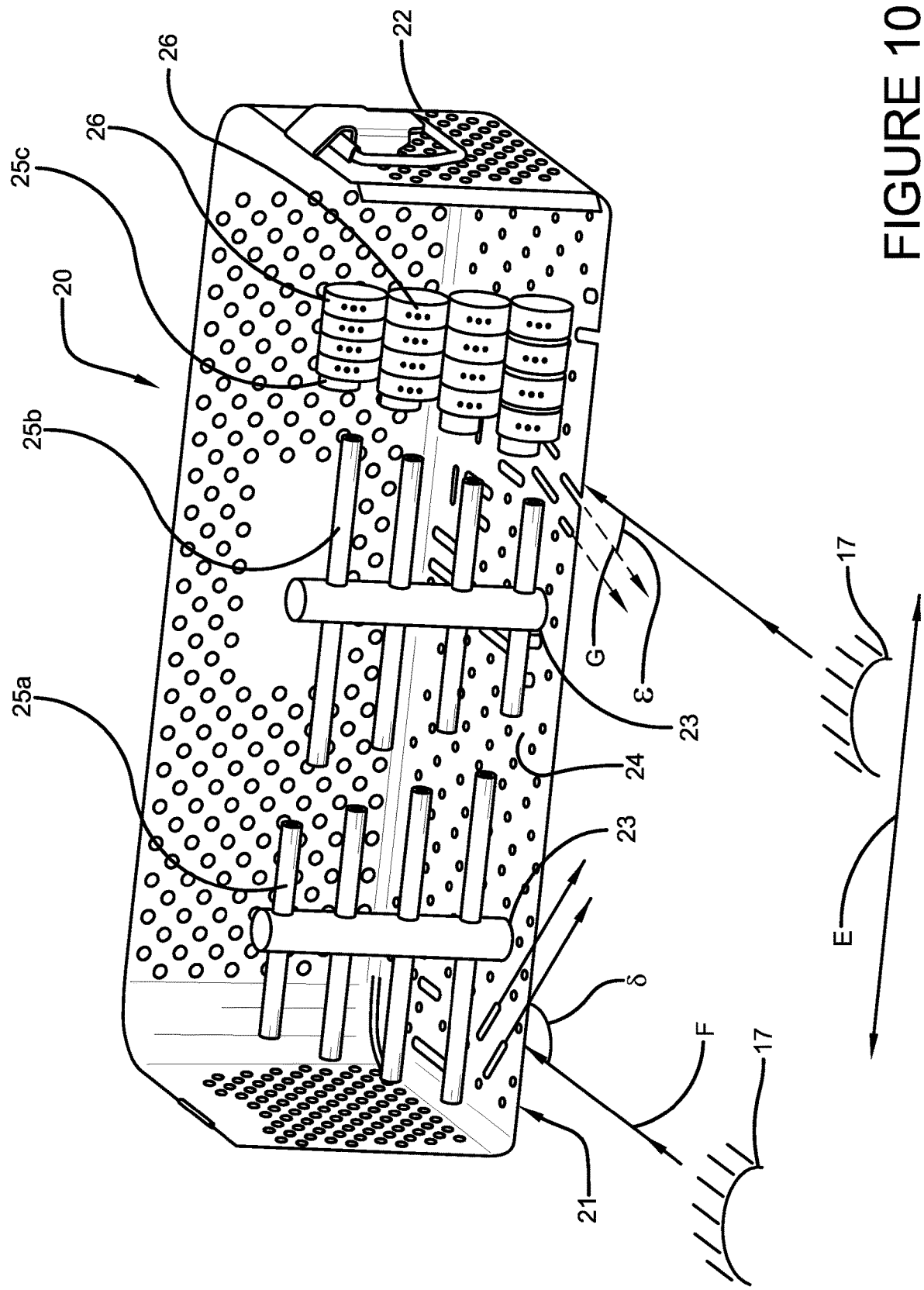
FIG. 10 illustrates a front perspective view of an implant carrier in accordance with the disclosed architecture.

FIG. 10 illustrates a front perspective view of another variant of the invention as may be used for the carriers 4, interbody cages, and the like. FIG. 10 illustrates an implant carrier 20 comprising a front surface 21 and a side surface 22. The implant carrier 20 further comprises a plurality of apertures 23 in a bottom surface 24 for positioning a plurality of implant racks 25A-C. The plurality of apertures 23 are arrayed in one or more series at an angle to the front surface 21 or the side surface 22 (such as arrayed along axes F or G at acute angles delta or epsilon, respectively, with respect to front surface 21) so as to allow the implant carrier 20 to be placed against an alignment surface or device so as to permit the user to scan a population of contained implants 26 hanging on the plurality of implant racks 25A-C with a source of reading illumination 27 (i.e., discernable by an imaging modality such as x-ray, fluoroscopy, computed tomography, electromagnetic radiation, ultrasound, visible light, UV light, magnetic resonance imaging, positron emission tomography and neutron imaging, etc.) that may be moved along or reciprocated along direction E. In this way, all of the plurality of implants 26 hanging on the plurality of implant racks 25Aa, 25B and/or 25C (which may be of different shape and/or with different number of extension arms or various sizes as exemplified by the implant racks 25A, 25B and/or 25C) may be conveniently read without some of the plurality of implants 26 eclipsing and thus obscuring other implants 26 in the array.

The alignment surface or device may be in the form of the interior surface of container 11 shown in FIG. 6 or the like, or that of a tray adapted to fit against the front surface 21 and the side surface 22, or even a surface associated with the illumination device itself, to provide alignment, typically approximately orthogonal alignment, to the reading illumination direction.

In this embodiment, the plurality of implants 26 may be of any shape amenable to being hung upon, distended over or otherwise captured by the implant racks 25A, 25B and/or 25C, such as ring-shaped as is the case of the plurality of implants 26.

It will appreciated that the plurality of implant racks 25A, 25B and/or 25C may be releasably maintained in the respective aperture 23 such as by a set screw or the like (not shown) to allow the plurality of implant racks 25 to be repositioned anywhere along the extend of the given aperture 23 and also turned within the given aperture 23 to allow the given implant rack 25A-C to have its hanging arms positioned beneficially with respect to the source of reading illumination 27, to allow, for instance, multiple implant racks such as the implant racks 25A-C, to be positioned and affixed to permit the implants supported thereupon to present a readable attitude to the source of reading illumination 27 in a spatially efficient fashion. For this reason, several series of apertures 23 may be used to accommodate any given number, size and shape of implant.

Figure 11:
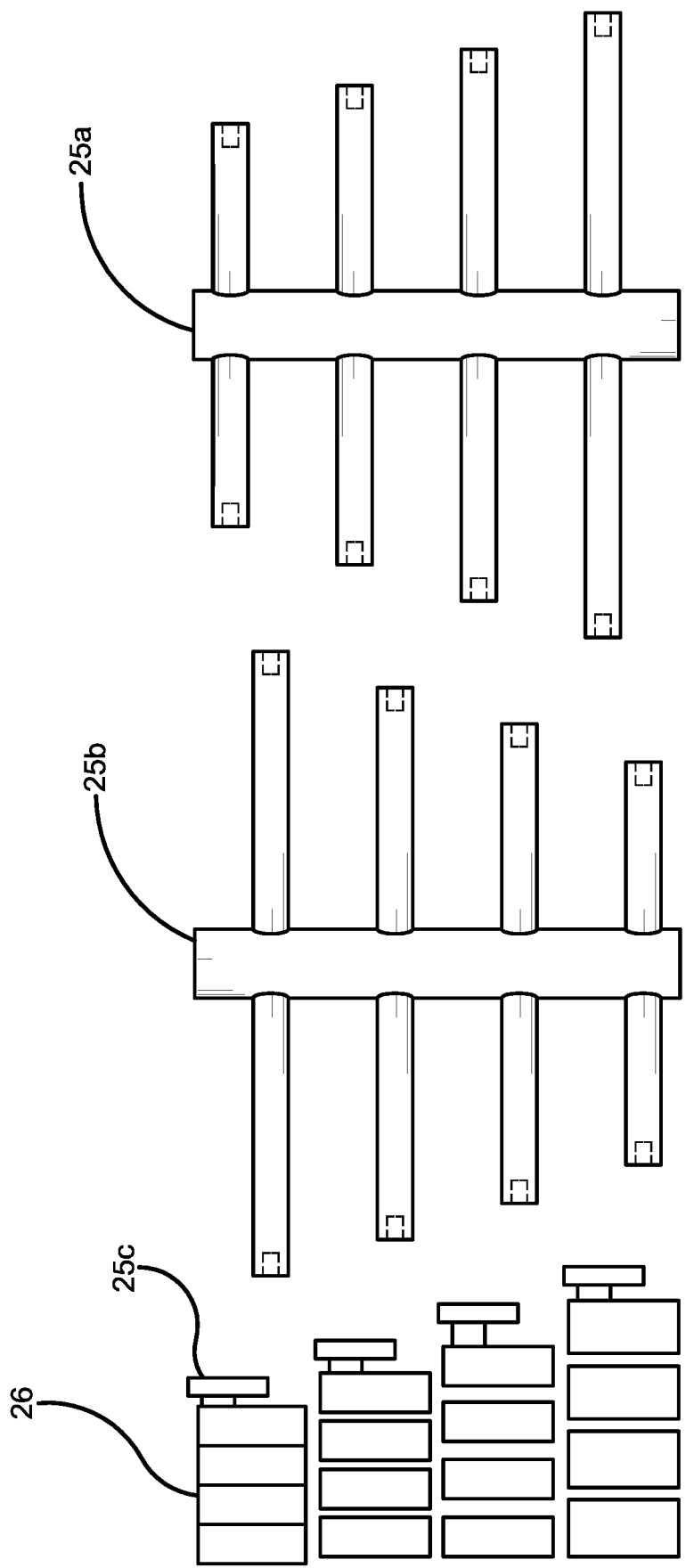
FIG. 11 illustrates an elevation view of a series of implant racks as they would appear when arrayed within the implant carrier in accordance with the disclosed architecture.

FIG. 11 is an elevation view of the series of implant racks 25A, 25B and 25C as they would appear when arrayed within the implant carrier 20. Interbody devices such as the plurality of implants 26 can be placed in the caddy or hung from the caddy bars (depending upon their geometry, such as curved, having angled sections or otherwise amenable to having their center of gravity supported by implant racks 25A, 25B and/or 25C) to have a clear view of the structurally encoded pins 2 from lateral X-ray images.

The plurality of implants 26 may be generally circular hollow implants suited to be hung upon implant racks 25a, 25b and/or 25c as shown in FIG. 10, such as those described in U.S. Provisional Application No. 62/204,233, filed Aug. 12, 2015, and U.S. patent application Ser. No. 15/235,914 filed Aug. 12, 2016 (both of which are incorporated herein by reference in their entirety) having a plurality of encoded readable elements, such as one or more orientation marker rods. The plurality of implants 26 may be manufactured using the same general method steps as described herein, such as by co-injection molding or additive manufacturing processes.

Figure 12:
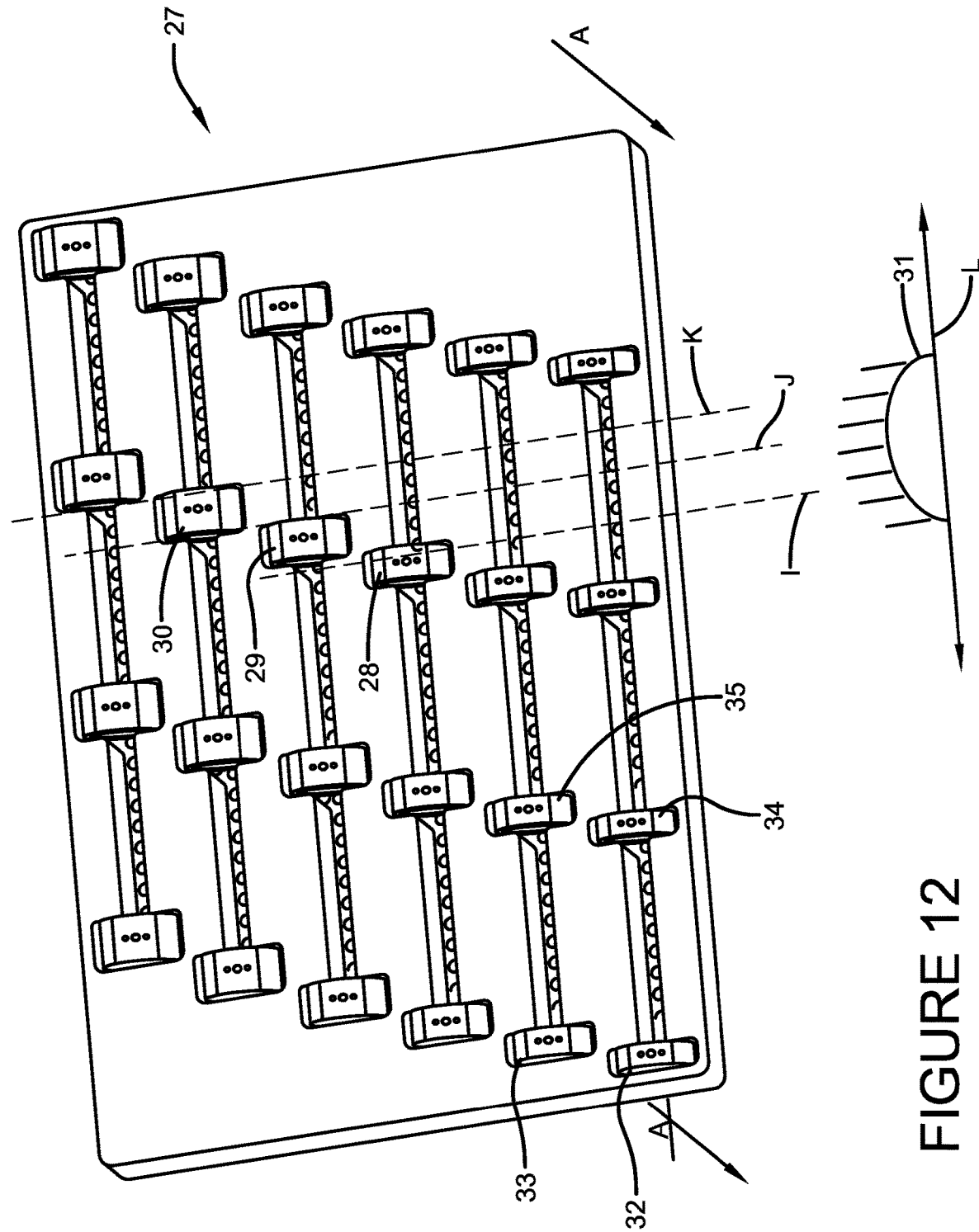
FIG. 12 illustrates a top perspective view of an implant carrier bearing a plurality of encoded implants in accordance with the disclosed architecture.

FIG. 12 illustrates a top perspective view of an implant carrier 27 bearing a plurality of encoded implants 28, 29 and 30 in accordance with another embodiment of the present invention. The implant carrier 27 holds the plurality of implants 28, 29 and 30 in a plurality of individual wells 32 such that a source of reading illumination 31 (i.e., discernable by an imaging modality such as x-ray, fluoroscopy, computed tomography, electromagnetic radiation, ultrasound, visible light, UV light, magnetic resonance imaging, positron emission tomography and neutron imaging, etc.) may be moved along or reciprocated along direction L. In this way, the plurality of implants 28, 29, 30 are maintained in a non-eclipsing series, such as along axes I, J, and K, each of which in turn contain four structurally encoded pins 2 similar to those described with respect to the elongate implants 1, and may be conveniently read without other of the implants eclipsing and thus obscuring other implants in the array.

Figure 13:
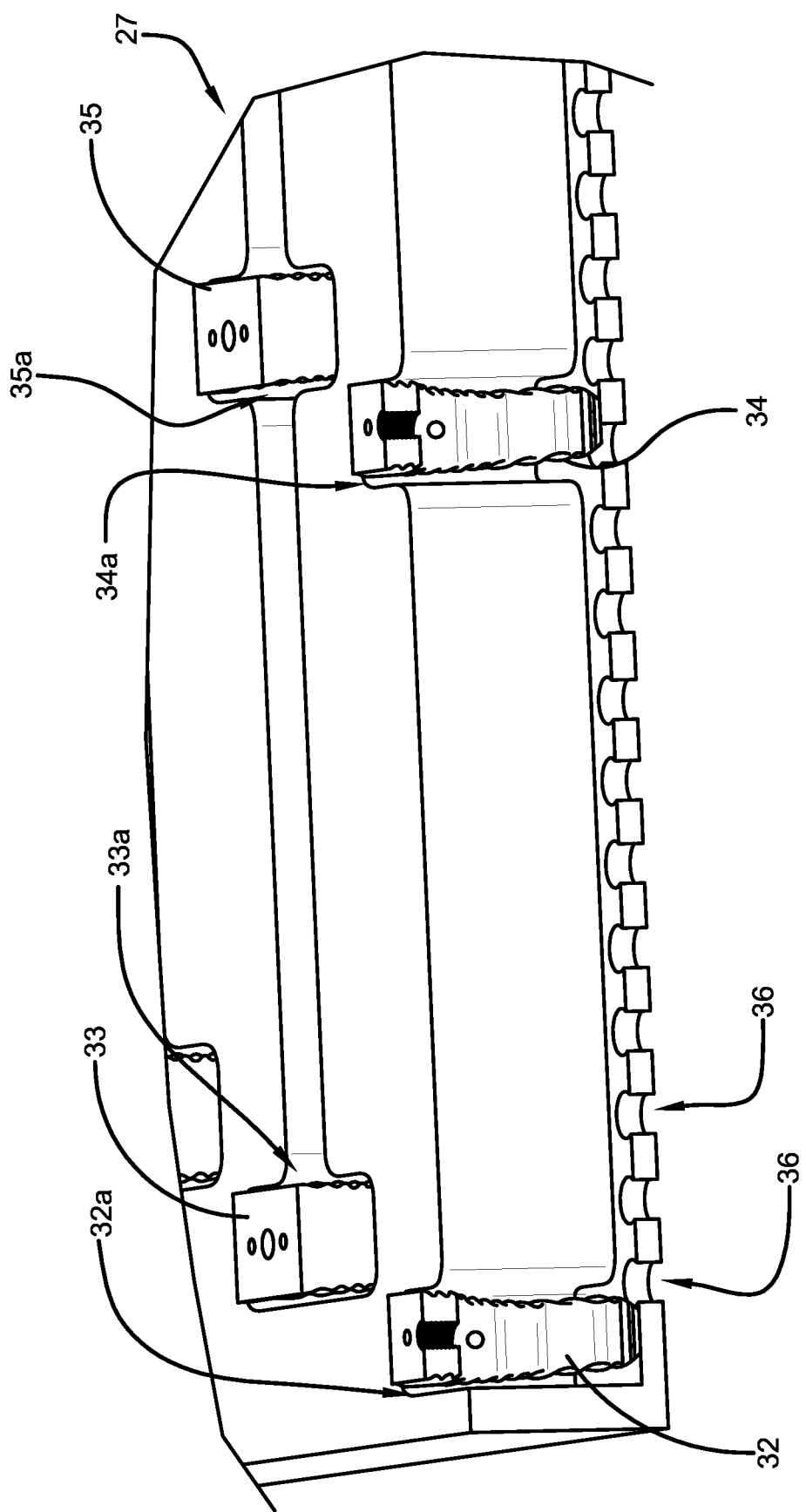
FIG. 13 illustrates a detailed partially sectioned top perspective view of the implant carrier bearing the plurality of encoded implants in accordance with the disclosed architecture.

FIG. 13 illustrates a detailed view of FIG. 12, partially sectioned along line A-A showing a top perspective view of the implant carrier 27 bearing a plurality of encoded implants 32, 33, 34 and 35 in a plurality of individual wells 32A, 33A, 34A and 35A, respectively. FIG. 13 also shows a plurality of apertures 36 that may be used to suspend the plurality of elongate implants 1 as described in the earlier FIGS. FIG. 13 further shows that the plurality of apertures 36 may be used to suspend a plurality of the pedicle screws as described supra.

Figure 14:
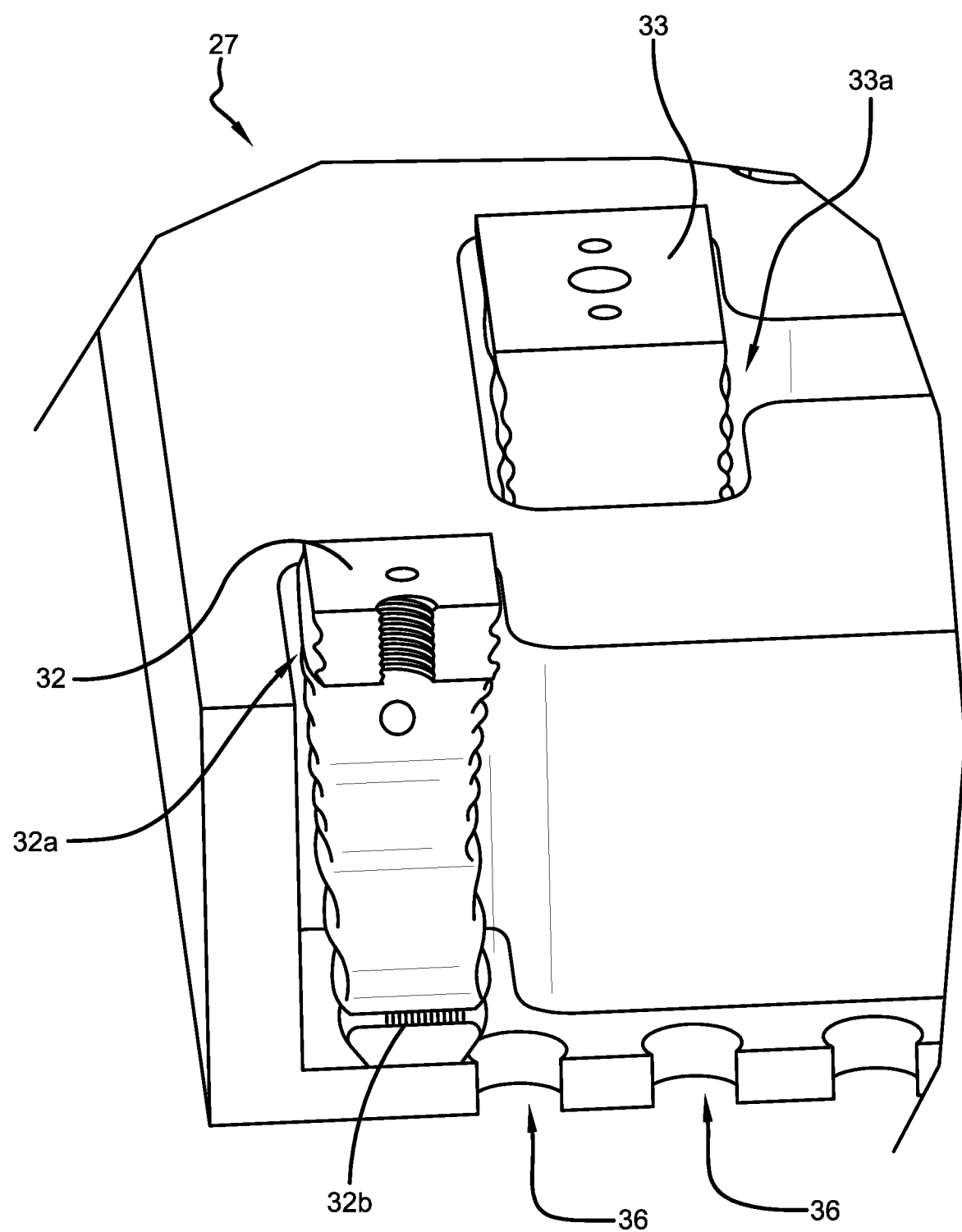
FIG. 14 illustrates a further detailed partially sectioned top perspective view of the implant carrier bearing the plurality of encoded implants in accordance with the disclosed architecture.

FIG. 14 illustrates a detailed view of FIG. 12, partially sectioned along line A-AA showing a top perspective view of the implant carrier 27 bearing the plurality of encoded implants 32 and 33 in the plurality of individual wells 32A and 33A, respectively. FIG. 14 also shows an encoded pin 32B which may become aligned in a non-eclipsed fashion by the placement of the plurality of encoded implants 32 and 33 in the plurality of individual wells 32A and 33A.

In one embodiment of the invention, an insert portion of an implant may be encoded with readable structurally encoded data through an electric discharge machining (EDM) processes. The encoded implant may then be encased, implanted, or otherwise contained within the implant.

Figure 15:
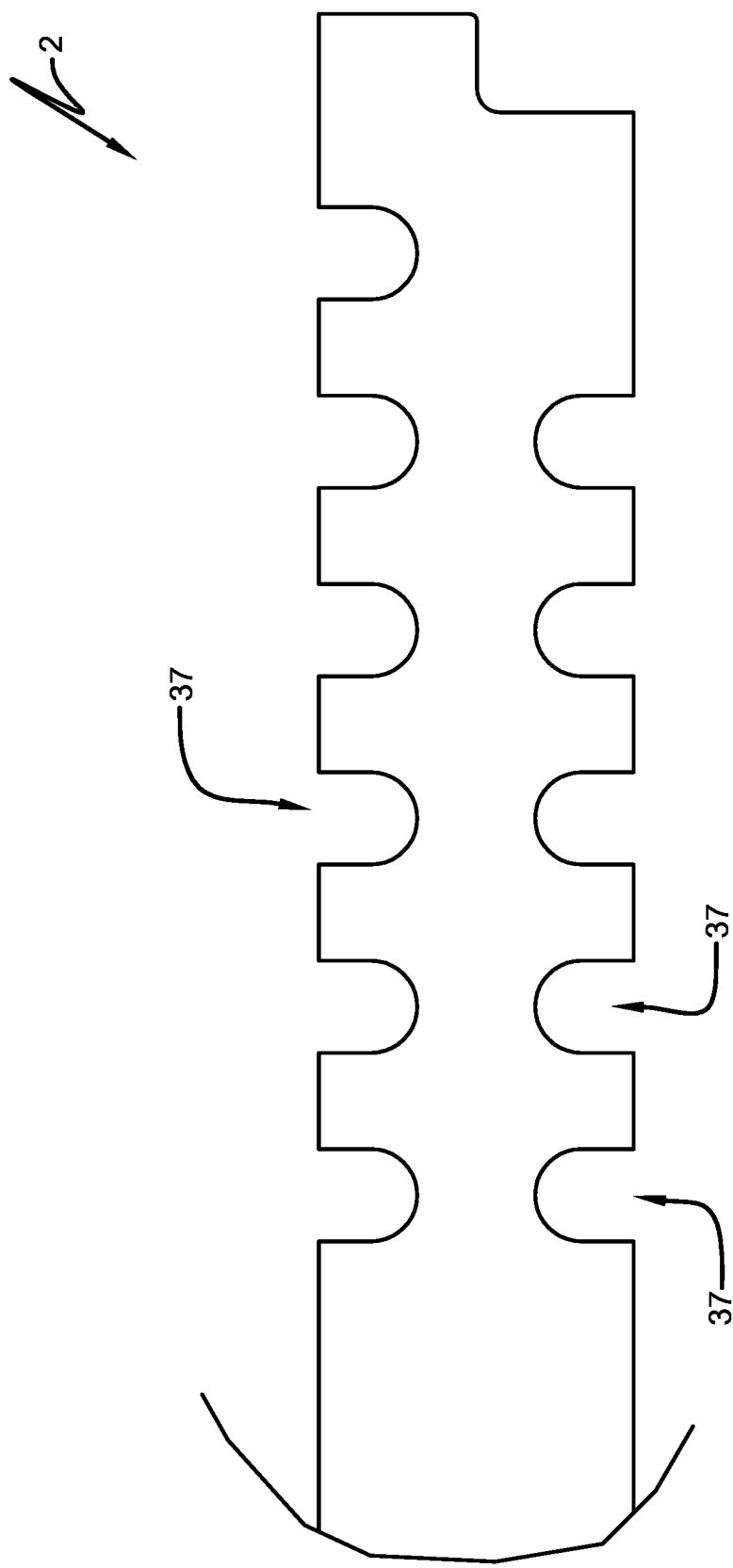
FIG. 15 illustrates a lateral view of an encoded implant in accordance with the disclosed architecture.

FIG. 15 illustrates a lateral elevation view of a series of the radio-opaque encoded pin 2. The radio-opaque encoded pin 2 may comprise a plurality of notches 37 placed in the encoded pin 2 through an electrical discharge machining (EDM) processes to produce arrays of wires or sinkers encoded with data. The plurality of notches 37 is exemplary of the plurality of surface characteristics representing the structurally encoded data.

The information or data encoded onto or into the implant devices of the embodiments disclosed in the present invention may be detected, decoded, read, transferred, stored, displayed, or processed according to such methods and devices disclosed in U.S. Pat. No. 8,233,967 or U.S. Patent Application Publication No. 2013/0053680, both of which are incorporated herein by reference.

The implantable devices such as the elongate implant 1 comprising the implant body defining the longitudinal axis or the circular implants 26 may be manufactured using additive manufacturing (AM) techniques, or using a combination of other molding or machining techniques (injection molding, machining, etc.) to produce the subject encoded implants. These additional techniques include without limitation material extrusion, vat photo polymerization, powder bed fusion, material jetting, binder jetting, sheet lamination and directed energy deposition.

The implantable devices used in accordance with the present invention may be manufactured by conventional methods such as a machining operation using any milling, lathe, or drilling operation to include standard machining and fabrication methods known in the art of manufacturing medical implants.

The present invention allows for the convenient, accurate and efficient reading of structurally encoded articles, which refers to the 3D encoding of digital information in a structure as variations in geometric or physical features—widths, densities, color, feature angles, etc. Bar codes are an example of a 2D encoding of digital information with modulations of color (dark versus light) with varying widths of printed bars on a surface. A typical embodiment of the structurally encoded devices of the present invention may contain data that is not readily apparent to a viewer of the device structure. Further, encoding of the typical embodiments of the present invention is handled by physical means other than those accomplished through circuitry, electromagnetic or other means, within the implant device itself or through a type of internal storage means such as magnetic storage means or the like. Such structurally encoded devices, as disclosed herein and described in relation to the typical and/or preferred embodiments of the present invention allow simplified production, maintenance, and/or operation costs for identification, storage, and/or retrieval of unique implant data while retaining a substantial amount of information with reduced probability for error.

The implant device carrier of the present invention enables better reporting, reviewing, inventorying and analyzing of implant devices to reduce medical error by enabling health care professionals and others to rapidly and precisely identify an implant device and obtain important information concerning the characteristics of the device, principally prior to installation. The present invention enhances analysis of devices on the market by providing a standard and clear way to document device use in electronic health records, clinical information systems, claim data sources, and registries.

It will also be appreciated that the present invention may be applied to similarly prepared articles such as articles that may benefit from structurally encoded structures as in the present invention. Such articles may include parts used in manufacturing, such as in the case of automobiles and parts therefor, firearms and parts therefor or jewelry and parts therefor.

The present invention also includes methods of reading the structurally encoded articles, as well as an inventory management system for structurally encoded articles that includes reading the encoded data from the encoded articles and storing the acquired data.

Other variations are within the spirit of the present invention. Thus, while the invention is susceptible to various modifications and alternative constructions, a certain illustrated embodiment thereof is shown in the drawings and has been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein. Variations of those preferred embodiments may become apparent to those of ordinary skill in the art upon reading the foregoing description. The inventor expects skilled artisans to employ such variations as appropriate, and the inventor intends for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An elongate implant comprising:
   an implant body defining a longitudinal axis and comprising an implant body longitudinal cannula extending through said implant body; and
   a structurally encoded pin contained within said implant body and aligned substantially along said longitudinal axis, said structurally encoded pin encoded through an electrical discharge machining process, wherein said structurally encoded pin comprises a pin longitudinal cannula and is contained within said implant body longitudinal cannula, and further wherein said implant body longitudinal cannula is substantially aligned with said pin longitudinal cannula.

2. The elongate implant of claim 1, wherein said structurally encoded pin comprises a plurality of characteristics representing structurally encoded data, said plurality of characteristics placed in said structurally encoded pin through the electrical discharge machining process.

3. The elongate implant of claim 2, wherein said structurally encoded data is discernable from outside the implant body via an imaging modality selected from the group consisting of x-ray, fluoroscopy, computed tomography, electromagnetic radiation, ultrasound, visible light, UV light, and magnetic resonance imaging.

4. The elongate implant of claim 1, wherein said elongate implant is selected from the group consisting of pedicle screws, rods and surgical pins.

5. A method of producing an elongate implant comprising:
   providing an implant body comprising an implant body longitudinal cannula extending through said implant body;
   preparing an insert portion of the elongate implant, said insert portion encoded with readable structurally encoded data relating to said elongate implant and encoded into said insert portion through an electric discharge machining process, wherein said insert portion is contained within said implant body longitudinal cannula; and
   positioning said insert portion within said elongate implant, wherein the insert portion comprises a pin longitudinal cannula that is substantially aligned with said implant body longitudinal cannula.

6. The method of claim 5, wherein the insert portion is a relatively radio-opaque structurally encoded pin.

7. The method of claim 5, wherein the elongate implant is selected from the group consisting of pedicle screws, rods, and surgical pins.

8. The method of claim 5, further comprising the step of directing an external source of reading illumination at said elongate implant.

9. The method of claim 8, wherein said external source of reading illumination is selected from the group consisting of x-ray, fluoroscopy, computed tomography, electromagnetic radiation, ultrasound, visible light, UV light, and magnetic resonance imaging.

10. The method of claim 8 further comprising the step of interpreting said readable structurally encoded data.

11. The method of claim 5, wherein the structurally encoded data is encoded into a shape of the insert portion.

12. The method of claim 5, wherein the structurally encoded data is encoded into a plurality of surface characteristics of the insert portion.

13. The method of claim 5 further comprising the step of storing said structurally encoded data.

14. A method of producing an implant comprising:
   encoding an insert portion of the implant with structurally encoded data through an electric discharge machining process; and
   encasing said insert portion within said implant, wherein the implant defines a longitudinal axis and comprises an implant longitudinal cannula extending through said implant, and further wherein said insert portion is aligned substantially along said longitudinal axis, comprises a pin longitudinal cannula, and is contained within said implant longitudinal cannula, and wherein said implant longitudinal cannula is substantially aligned with said pin longitudinal cannula.

15. The method of claim 14 further comprising the step of directing an external source of reading illumination at said implant.

* * * * *